United States Patent
Bures

(10) Patent No.: US 6,877,361 B2
(45) Date of Patent: Apr. 12, 2005

(54) VISCOSIMETER

(75) Inventor: Klaus-Dieter Bures, Berlin (DE)

(73) Assignee: WGE Dr. Bures GmbH & Co. KG, Dallgow (DE)

( * ) Notice: Subject to any disclaimer, the term of this patent is extended or adjusted under 35 U.S.C. 154(b) by 0 days.

(21) Appl. No.: 10/718,945

(22) Filed: Nov. 21, 2003

(65) Prior Publication Data

US 2004/0134262 A1 Jul. 15, 2004

Related U.S. Application Data

(62) Division of application No. 09/974,706, filed on Oct. 10, 2001, now Pat. No. 6,708,553.

(30) Foreign Application Priority Data

Apr. 30, 2001 (EP) ............................................. 01110629

(51) Int. Cl.[7] ............................................... G01N 11/04
(52) U.S. Cl. ..................... 73/54.04; 73/54.05; 73/54.06; 73/54.09
(58) Field of Search ............................ 73/54.04, 54.05, 73/54.06, 54.09, 54.11, 54.14

(56) References Cited

U.S. PATENT DOCUMENTS 3,808,877 A * 5/1974 Blair .......................... 73/54.06
4,384,792 A * 5/1983 Sommers et al. ............. 374/36

FOREIGN PATENT DOCUMENTS

| EP | 113560 | * 7/1984 | ................ 73/54.09 |
| EP | 181224 | * 10/1985 | ................ 73/54.06 |

* cited by examiner

*Primary Examiner*—Daniel S. Larkin
(74) *Attorney, Agent, or Firm*—Friedrich Kueffner

(57) ABSTRACT

A viscosimeter for measuring the viscosity of a solution in a solvent includes flow resistances having the smallest possible thickness and a small volume compared with all other parallel and following capillaries in a flow conduit system with two legs. The flow conduit system has three parallel flow circuits among which at least two flow circuits are connected by a differential pressure sensor or sensor for differential pressure. The arrangement includes an inlet which divides into two legs, wherein one of the two legs includes a pressure reducing element, a following branch going to a differential pressure sensor and a pressure reducing element in the feeding conduit to a junction which runs into an outlet conduit. The other leg starting from the branch point includes a pressure reducing element which is connected to the differential pressure sensor and to a resistance capillary in the conduit.

8 Claims, 18 Drawing Sheets

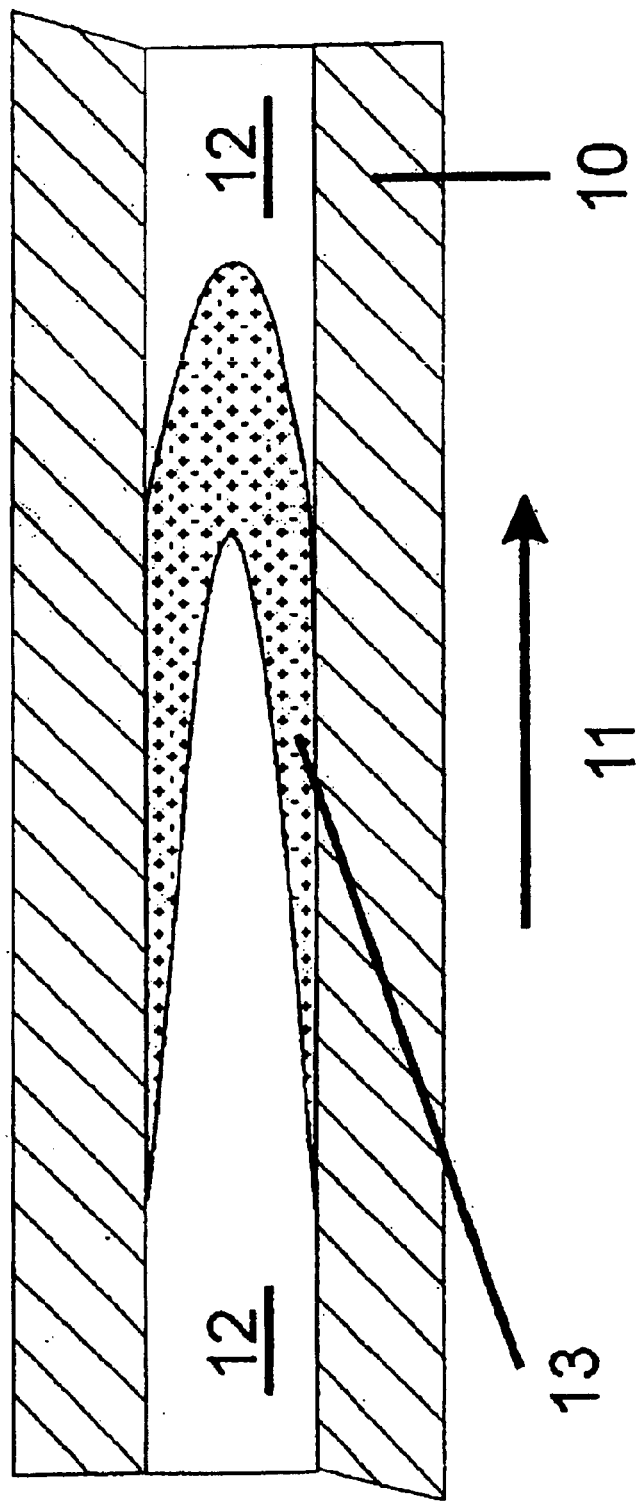

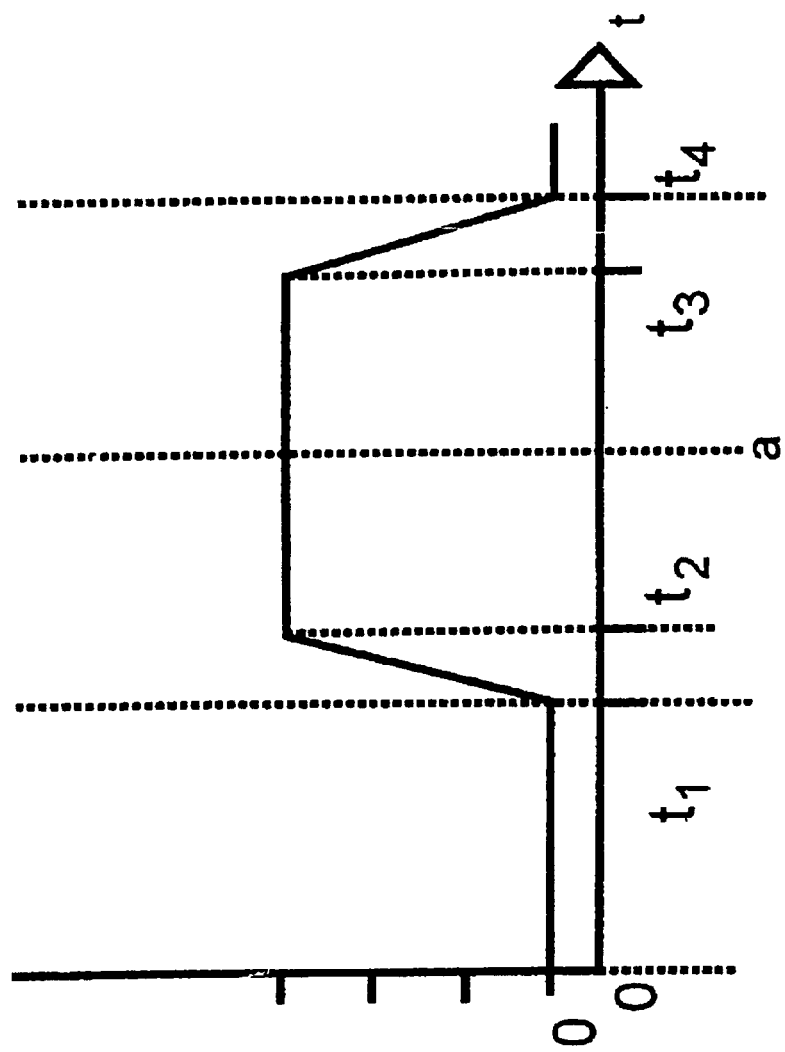

Fig.15

$$\eta = \frac{\pi \cdot R^4}{8 L} \cdot \frac{\Delta P}{Q} \quad (1)$$

$$\dot{\gamma} = \frac{4}{\pi \cdot R^3} \cdot Q \quad (2)$$

$$\sigma = \frac{R}{2L} \cdot \Delta P \quad (3)$$

$$I = Q = A_1 \cdot \sqrt{\frac{2 \cdot \Delta P}{1 - \left(\frac{A_1}{A_2}\right)^2} - 1} \quad (4)$$

VISCOSIMETER

CROSS-REFERENCE TO RELATED APPLICATIONS

This application is a Divisional Application of U.S. patent application Ser. No. 09/974,706 filed Oct. 10, 2001 now U.S. Pat. No. 6,708,553.

BACKGROUND OF THE INVENTION

1. Field of the Invention

This invention relates to a viscosimeter for measuring the relative intrinsic or inherent viscosity of a solution in a solvent.

2. Description of the Related Art

According to the state of the art, the difference is made between the relative, the specific as well as the inherent viscosity and finally the limiting viscosity number (intrinsic viscosity). By relative viscosity, we understand the quotient of the viscosity of the solution, for example of a polymer, to the viscosity of the pure solvent. The inherent viscosity results as the quotient of the natural logarithm of the relative viscosity divided by the concentration in grams of the dissolved substance per millimeter solution. There results herefrom the intrinsic viscosity as a limiting value of the inherent viscosity for the case that the aforesaid concentration goes towards zero. The so-called Hagen-Poiseuille's formula is fundamental for viscosity measures. According to the state of the art, individual capillary measures are known for which the volume rate of the solution flow and the flow pressure drop are measured and, the geometric dimensions of the capillary being known, the viscosities of the examined liquids can be determined herefrom. The disadvantage of this measuring method consists in the unfavourable signal-to-noise ratio. The noise is essentially produced by high-frequency interfering signals of the pump which is required for conveying the substance to be examined. Moreover, irregular flow rates of the substance including the counter-pressure fluctuations produce interfering signals on flow resistances. Finally, it is known that the viscosity is of course temperature-dependent, for which reason variations of temperatures during the measure can distort the measuring result.

According to the U.S. Pat. No. 3,808,877, to solve this problem, a flow limiter is used between the solvent feeding point and the measuring capillaries to produce a constant flow rate. The relative viscosity is determined by separate measures of the pressure drop on the capillary for the direct flowing polymer solutions and for the pure solvent. From this printed document, a device of two capillaries in parallel running legs is also known, one of them being filled with the polymer solution and the other one with the solvent. Basically, separated measures of said substances are also possible in such a way that the first substance flows through the first capillary and the second substance through the second capillary of a conduit during the measuring, whereby these capillaries are connected in series the one behind the other. The condition for carrying out an exact viscosity determination is in particular the geometric coincidence of the diameter and of the length of the used capillaries, likewise a temperature uniformity at the measuring points.

According to the EP 0 181 224, a capillary viscosimeter is proposed with two capillaries connected in series for which the one serves as a reference capillary only for the solvent and the second as an analysis capillary for the polymer solvent solution. The capillaries consist of long thin tubes into which the solvent is introduced through a pump. A resistance path in form of a tube with a small diameter is between the pump and the reference capillary which serves to produce a counterpressure. A further pulse attenuator can eventually be added to this resistance path. The differential pressure measured in the reference capillary (pressure drop) is supplied to a differential amplifier or to an evaluating unit just as the pressure drop which is measured on the analysis capillary. The feeding point for the substance to be examined, for example a polymer, is between the reference capillary and the analysis capillary so that the analysis capillary is traversed by a solution consisting of the polymer and the solvent. This arrangement connected in series can be changed as far as the feeding point for the test substrate can also be situated before the first capillary.

In this case, the first capillary becomes the analysis capillary. After having passed through it, the solution flows into a retaining vessel which assumes the function of diluting the solution further so that substantially only the solvent is measured by the reference capillary. In the described arrangement, a gel permeation chromatograph can be placed between the feeding point, for example for the polymer, and the analysis capillary, chromatograph in which polymer substances can be separated in a dilution solution according to their molecular size.

Besides the series connection described above, capillary bridge viscosimeters are also still known which are characterized by a relatively high sensitivity. In the bridge connection, a conduit is separated into two parallel running conduit parts in which there are respectively two capillaries connected in series. A place situated between the respectively first and the second capillary of each leg is connected with the corresponding place of the other leg over a connection conduit in which a high sensitive pressure sensor is placed.

According to the embodiment described in the EP 0 113 560, a retention basin in form of a switchable bypass device is moreover provided for before the second capillary of a leg. As far as all existing four capillaries are flown through by the same liquid—and in particular without including the bypass—the connection conduit remains unpressurized. However, if a storage tank is placed above the bypass conduit, the second measuring capillary is substantially only flown through by the solvent so that there results a pressure drop with respect to the other measuring leg because of the different viscosities of the liquids. This pressure drop can be recorded and can be used for determining the viscosity.

Moreover, from the EP 0 083 524, we still know devices with only one capillary which are supposed to have a length of several meters for a diameter between 0.2 and 0.3 mm. This capillary with a total length of, for example 3 mm, is wound in form of a loop with a diameter of at least 10 cm.

SUMMARY OF THE INVENTION

The aim of this invention is to improve the device mentioned in the introduction in order to avoid the detector dispersion appearing until now because of the used capillaries or to considerably reduce it and thus to increase the measuring accuracy of the device so that the least pressure differences are measurable.

According to one embodiment of the invention, a flow resistance with the smallest possible volume is used in the sample flow leg (hereunder designated as KV flow resistance), this flow resistance being placed directly behind the feeding point of the flow division. Accordingly, the viscosimeter shows flow resistances, such as disk-shaped or leaf-shaped Venturi nozzles or different KV flow resistances, with the smallest possible thickness and with a small volume with respect to all other parallel and following capillaries in a flow conduit system with two legs. This flow conduit system contains in the first leg at least three pressure reducing elements, for example capillaries, whereby behind the capillary following the branch point a pressure manometer is provided for with a connected bigger vessel, whereby behind further capillaries connected with each other with different diameters and with a big volume which corresponds to 100 to 1000 times the KV flow resistance in the second leg, a branch point leads to a differential pressure sensor or a sensor for differential pressure followed by capillaries with different diameters connected with each other up to the junction in a common outlet conduit. In the second leg, the KV flow resistance follows the branch point, this resistance being followed by further big volume conduits which lead to the branch point of the opposing side of the differential pressure sensor or of the sensor for differential pressure, whereby further capillaries connected with each other with different diameters and with different lengths follow the branch point, these capillaries joining into the common outlet conduit.

The viscosimeter comprises an inlet which runs into a junction from which the one capillary in one first leg leads over a big distance and with a comparatively big volume to a manometer (absolute pressure manometer) and from this to a still bigger vessel which has a 100 times to 1000 times bigger volume than the volume of the KV flow resistance in the second leg, a connecting conduit leading from the vessel to a pressure reducing element which is a capillary, a nozzle, a frit or an appropriate supplying conduit which reduces the pressure in the flow conduit. The pressure reducing element is connected over a connection with a further capillary with a big volume which runs into the branch point, whereby the differential manometer or the sensor for differential pressure placed in the connecting conduit between the two branch points in both legs measures high sensitively the slightest pressure differences between the two branch points of the flow conduit. The big volume capillary following the connecting point leads over a connection to a further pressure reducing capillary, whereby the pressure reduction must not be identical with that in the upper section of the flow conduit. A connecting conduit follows the capillary into the junction of both legs to a common outlet conduit which makes possible the common discharge of the solvents from different flow lines. From the branch in the second leg, a pressure reducing element which can have different configurations leads directly into a big volume vessel and from there into a conduit with a big internal diameter which is connected by the branch with the differential manometer or differential pressure sensor, whereby the differential pressure sensor is switched here in such a way that it generates a positive signal for a pressure drop at the branch point, a conduit with a big internal diameter following the branch point, this conduit being connected over the connection with a pressure reducing capillary and constituting the access to the junction and to the outlet conduit.

The viscosimeter according to another embodiment also shows flow resistances, such as disk-shaped or leaf-shaped Venturi nozzles or different KV flow resistances, with the smallest possible thickness and with a small volume with respect to all other parallel and following capillaries in a flow conduit system with two legs. Unlike the viscosimeter according to the first embodiment, the flow conduit system shows three parallel flow circuits among which at least two flow circuits are connected by a differential pressure sensor or sensor for differential pressure. These three flow circuits constitute an analogy to the Thompson bridge. The arrangement itself consists of an inlet which runs into a branch and divides into two legs, whereby one of the two legs comprises a pressure reducing element, a following branch point to a differential pressure sensor or to a sensor for differential pressure and a reducing element in the feeding conduit to a junction which runs into an outlet conduit. The other leg starting from the branch point comprises a pressure reducing element which leads to a branch which first leads into a big volume vessel leading to a junction and second which leads to a resistance capillary which is connected in the junction with the differential pressure sensor or the sensor for differential pressure and which is furthermore connected with a resistance capillary in the conduit lead from the junction to a further junction, whereby the resistance capillary is connected on the outlet side over the junction with a pressure reducing element which runs over a conduit section into the junction and thus into the outlet conduit.

The invention according to another embodiment consists in that the viscosimeter shows flow resistances, such as disk-shaped or leaf-shaped Venturi nozzles or different KV flow resistances, with the smallest possible thickness and a small volume compared to all other parallel and following capillaries, whereby these flow resistances are placed directly behind the feeding points of the flow division and in the other partial leg behind the flow division there follows a long conduit with a big internal diameter which is furthermore more precisely defined by the fact that the capacity of this long tube amounts to 100 to 1000 times the KV flow resistance.

The KV flow resistance can be a very short capillary piece with a small internal diameter which is considerably lower than all other following or parallel running capillaries, a so-called microsystem technique component, for which engravings are built into the silicium basic material by photolytic methods and which can be connected in combination with external macroscopic flow resistances with viscosimeters according to the invention.

Furthermore, a KV flow resistance can also be created in that the flow resistance can be used, for example, in the form of disk-shaped or leaf-shaped Venturi nozzle bodies with the smallest possible thickness. Here, the low spatial or volumetric dimension is decisive, which is advantageous in that, because of the favorable ratio of volume, the sample can be decomposed into nearly infinitesimal signal sizes in time and thus a systematic enlarging of the measuring signals through the measuring system, as it is observed for all measuring cells used according to the state of the art, is avoided. This enlarging had to be corrected, for example mathematically, up to now as far as this was possible. Further configurations of the viscosimeter are also possible. For example, in the case of the Venturi nozzle body, the thickness should be smaller or bigger than 2 mm, preferably 2 mm or 3 mm. Preferably, the Venturi nozzle body flow opening is circular or slit-shaped. Alternatively, the nozzle body can however also have several hole-type openings of $1\mu$ to $10\mu$. The channels of the microsystem technique components can have structures with a width of $10\mu$ to $100\mu$. The same is valid for so-called fused silica capillaries and capillaries with which corresponding ratios of volume can be realized because of their internal diameter.

Basically, the KV flow resistance according to the invention can be used in all viscosimeters in which capillaries have been used until now. However, because of the high measuring accuracy which can be achieved, a bridge arrangement is chosen with two parallel running flow paths in which, among respectively three flow resistances placed the one behind the other, one KV flow resistance is at least respectively in one leg. Apart from that, the bridge arrangement known from the state of the art and described for example in the EP 0 113 560 can be gone back to.

Moreover, preferably a KV flow resistance, for example a Venturi nozzle or a microsystem technique channel is directly behind a gel permeation chromatography column, this being seen in flow direction, which is fundamentally known according to the state of the art with respect to its structure as well as to its mode of operation and which is already used for example in a viscosimeter arrangement according to EP 0 181 224.

With respect to Venturi nozzles existing the one behind the other or in a branched bridge arrangement, a big volume retention basin can be provided for in the supply network for increasing the measuring speed. The function of these retention basins is basically known by the state of the art from the aforesaid printed documents, in series arrangements as well as in bridge arrangements.

For checking or for the further detection, it can be advantageous to place a refraction detector or a membrane osmosis detector in the supply network. Further detectors are conceivable in specific combinations and represented in FIGS. 12 to 14.

For avoiding temperature variations and thus for increasing the measuring accuracy, it is finally recommended to place the whole supply network in a thermally constant closed space, preferably in a thermally adjustable heat bath. The invention will be explained in detail below with reference to concrete embodiments.

BRIEF DESCRIPTION OF THE DRAWINGS

FIG. 1A shows the flow profile of a sample with a high flow rate or a high molecular weight.

FIG. 2 shows the signal course of a sample which flows through the cell with a rectangular flow profile.

FIG. 15 is an annex with formulae.

DETAILED DESCRIPTION OF THE INVENTION

Figure 1:
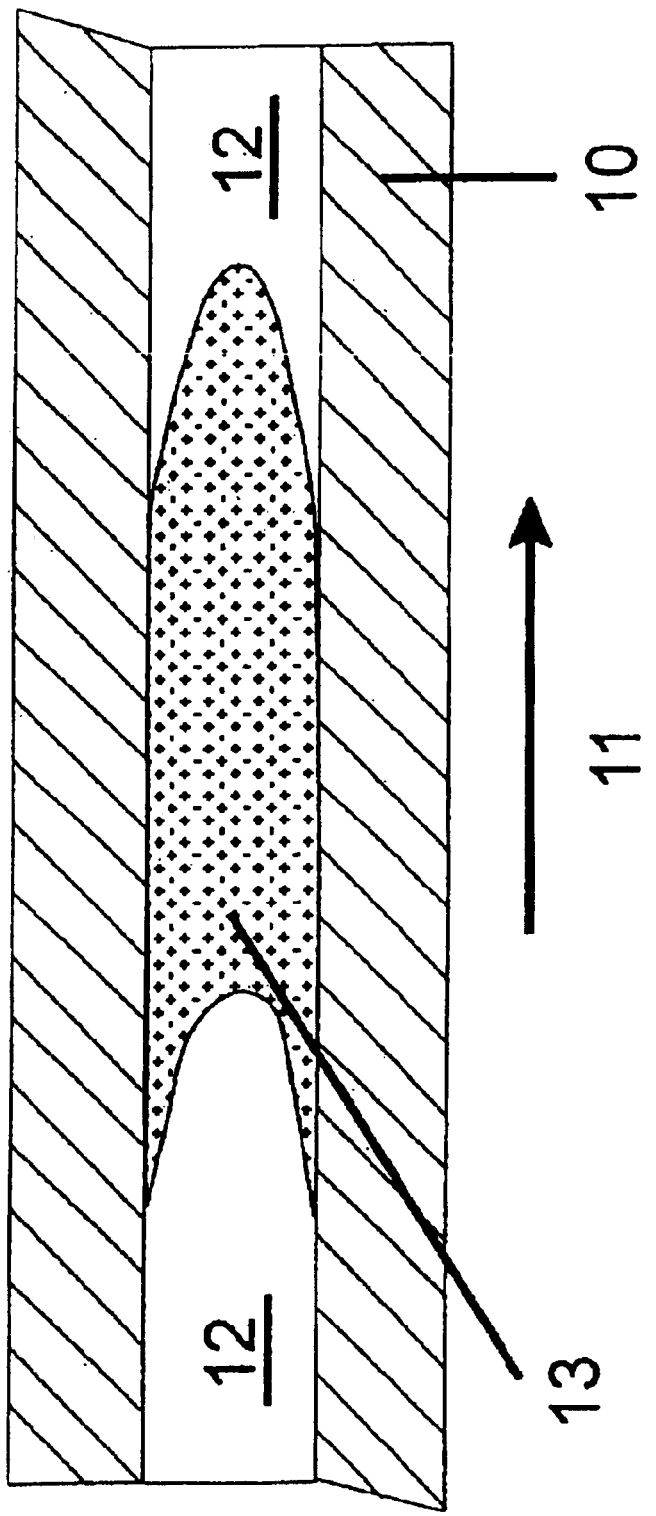
FIG. 1 shows the flow profile of a sample in a capillary.

When a capillary 10 is flown through by a liquid in direction of a part 11 represented in FIG. 1, it shows the parabolic flow profile known according to the state of the art. As may be seen in FIG. 1, this is also valid for the case that a sample 13 is given into an eluent 12, for example, in form of a drop.

For a finite layer thickness of a cell 10 and an ideal sample with a rectangular flow profile, there results the signal course represented in FIG. 2 for which at the time t1the sample enters the cell, whereby there is a mixture between the sample and the eluent in the cell up to the time t2. From the time t2, the sample fills the cell completely, namely until the time t3 from which the eluent 12 is charged later. At the time t4, the sample 13 has completely left the cell, there is only the eluent therein.

Figure 3:
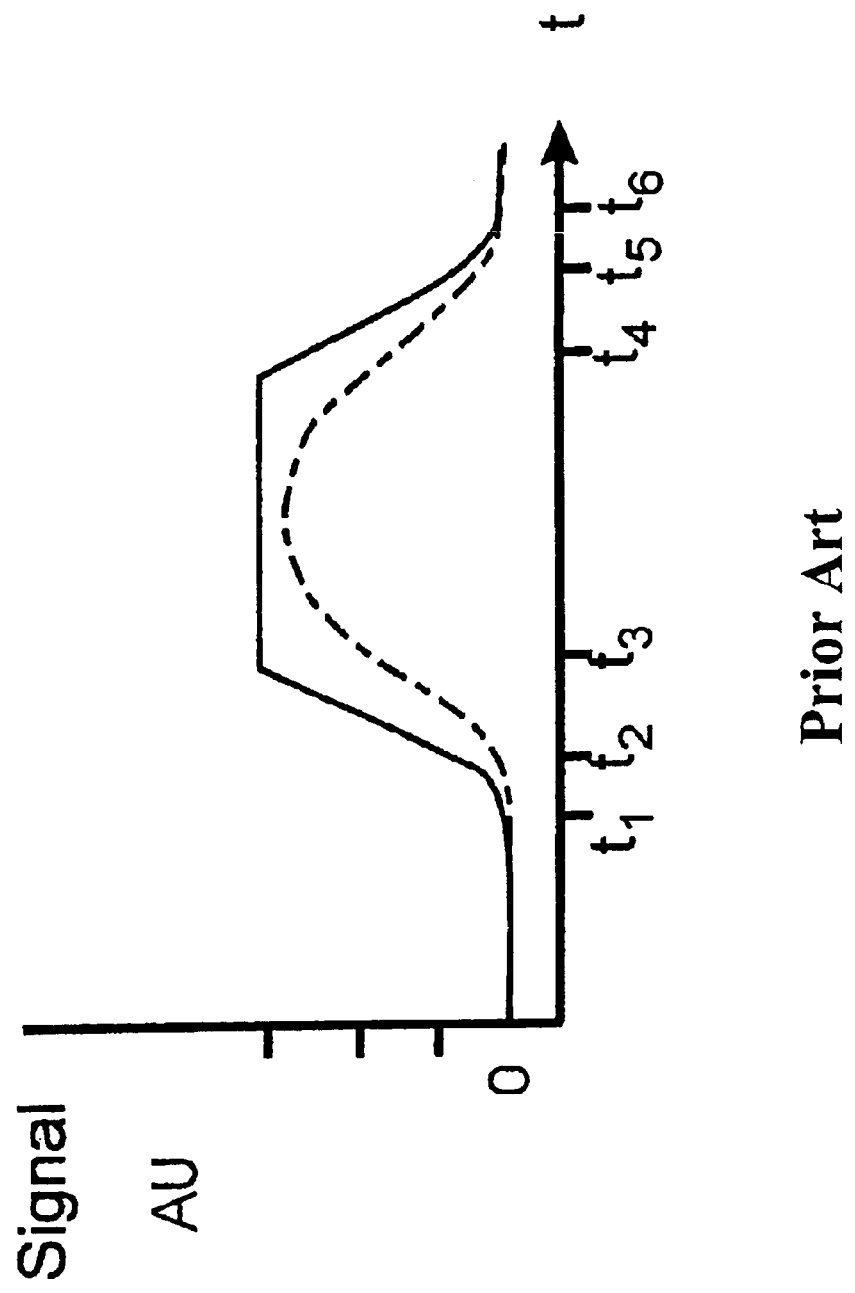
FIG. 3 shows a curve course according to FIG. 2 by considering the real flow profile of a sample as well as in dotted lines by considering the flow profile represented in FIG. 1A.

If we consider the real flow profile according to FIG. 1, there results the signal course which can be seen in FIG. 3 in which during the period between t1 and t2 the sample 13 with its parabolic front flows into the cell. The same is valid by leaving the sample 13 with respect to the period between the times t5 and t6 in which the curve course is not linear. Due to this curve course which is not linear, the analysis is however considerably complicated. A further complication appears when, in case of high flow rates and samples with a high molecular weight with a corresponding concentration, a flow profile according to FIG. 1A is constituted. For these cases, there results the signal course represented in dotted lines in FIG. 3 which only allows relative relations.

Figure 4:
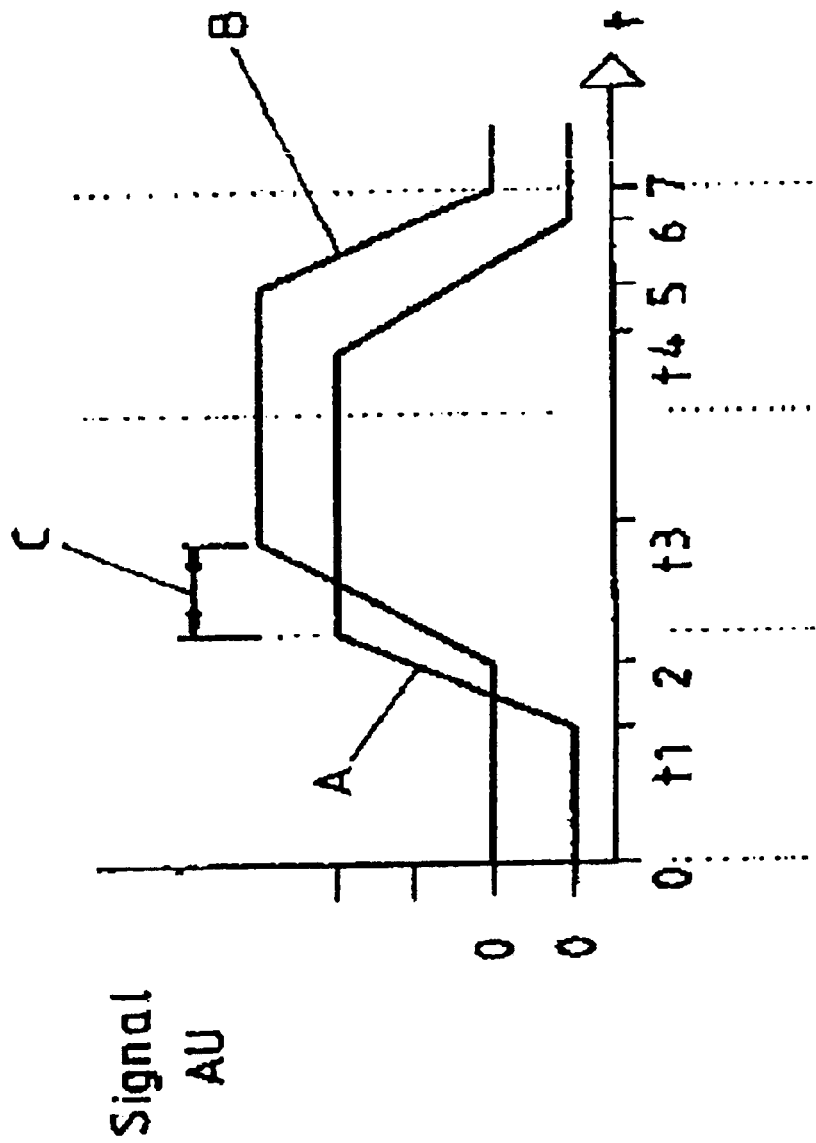
FIG. 4 shows a representation of two measuring signals of different detectors with a different layer thickness.

The signal is completely insoluble when two detectors emit output signals A and B which have, for example, the idealized time history represented in FIG. 4. It comes regularly to a so-called offset C of the detectors because of the distance differences for the sample stopper 13. Moreover, there results, because of different layer thicknesses of the cells 10, a different edge steepness of both signals A and B.

The different times concern the following states:

t1: The sample enters the cell 10 of the first detector.

t2: The cell 10 is fully filled, the sample 13 enters the second cell.

t3: The second cell is also fully filled.

t4: The sample leaves the first cell.

t5: The sample leaves the second cell.

t6: The first cell is fully filled again with eluent and t7: the second cell is also filled with eluent. The parabolic form of the flow profile is not yet taken into account, what leads to a further complication for a signal course, as represented in FIG. 3.

Apart from the different signal courses, there remains, in the analytic practice, further the problem that in many cases no plateaus are constituted what results in that intrinsic properties and systematic errors cannot be distinguished any longer.

Figure 5:
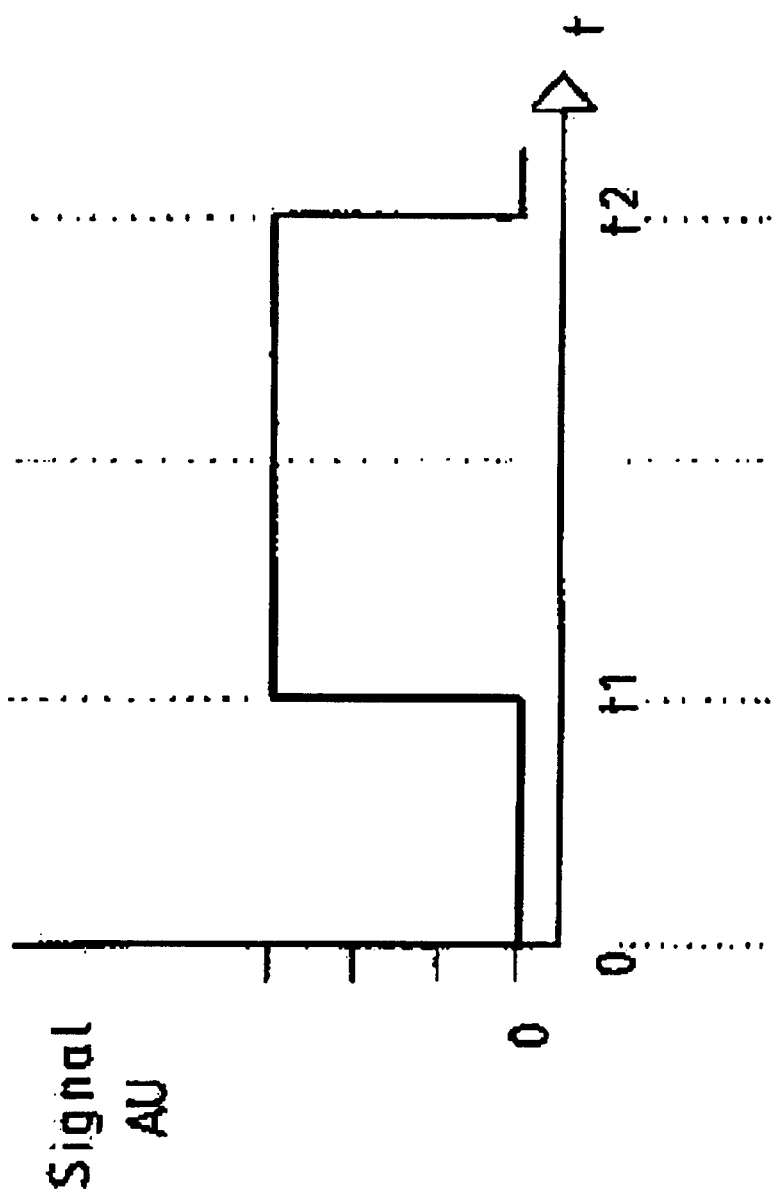
FIG. 5 shows the signal course by using a KV flow resistance according to the invention.

This invention remedies, as FIG. 5 shows with the curve for a viscosimeter with a small thickness of the KV flow resistance. The times t1 and t2 represent the inlet of the sample 13 into the KV flow resistance or the outlet of the sample thereof. Before and after these times t1 and t2, the eluent is respectively in the KV flow resistance. As may be seen in FIG. 5, we obtain not only quasi signal rectangular courses, i.e. the omission of the leading edges and of the trailing edges, but in the case of the use of two detectors, also definite resolution possibilities. This also results from the following theoretical considerations:

The pressure drop which is registered by the pressure sensors is related to the viscosity by the following known relations:

$$n = \frac{\pi \cdot R^4}{8 \cdot L} \cdot \frac{\Delta P}{Q} \quad (1)$$

$$\dot{\gamma} = \frac{4}{\pi \cdot R^3} \cdot Q \quad (2)$$

$$\sigma' = \frac{R}{2 \cdot L} \cdot \Delta P \quad (3)$$

$$I = Q = A_1 \cdot \sqrt{\frac{2 \cdot \Delta P}{l \cdot \left[\left(\frac{A_1}{A_2}\right) - 1\right]}} \quad (4)$$

Here, n=viscosity of a Newton liquid
L=thickness of the KV flow resistance
A=cross section of the flow opening (or frit pore)
R=radius of the opening (or frit pore)
Q=flow rate through the opening and
p=pressure drop at the opening over the thickness (or the direct flow length)

Unlike the capillary viscosimeter according to the state of the art, the Venturi equation stated above as equation 4 is included in the viscosity definition according to the equation 1. Thus, the error resulting of the different frictional force which appears in capillary viscosimeters is avoided, what is clear by the following conversion of the equation 1:

$$F_r = R^2 \pi \Delta p$$

Along the way that a sample covers in a capillary, there results a different frictional force as well as other shearing forces so that, despite a supposed homogeneity of the probe, the detected pressures are different. On the other hand, with this invention, it is not a mean value of the pressure difference which is constituted, as it is usual for capillary measurements, but the pressure respectively corresponding with the viscosity is exactly indicated.

The KV flow resistance can principally also be configured as a frit, a filter or a membrane, as far as it constitutes a flow channel taper and it simultaneously possesses the smallest possible thickness (or length).

The arrangement of the KV flow resistances in different assemblies can be seen in FIG. 6 to 14.

Figure 6:
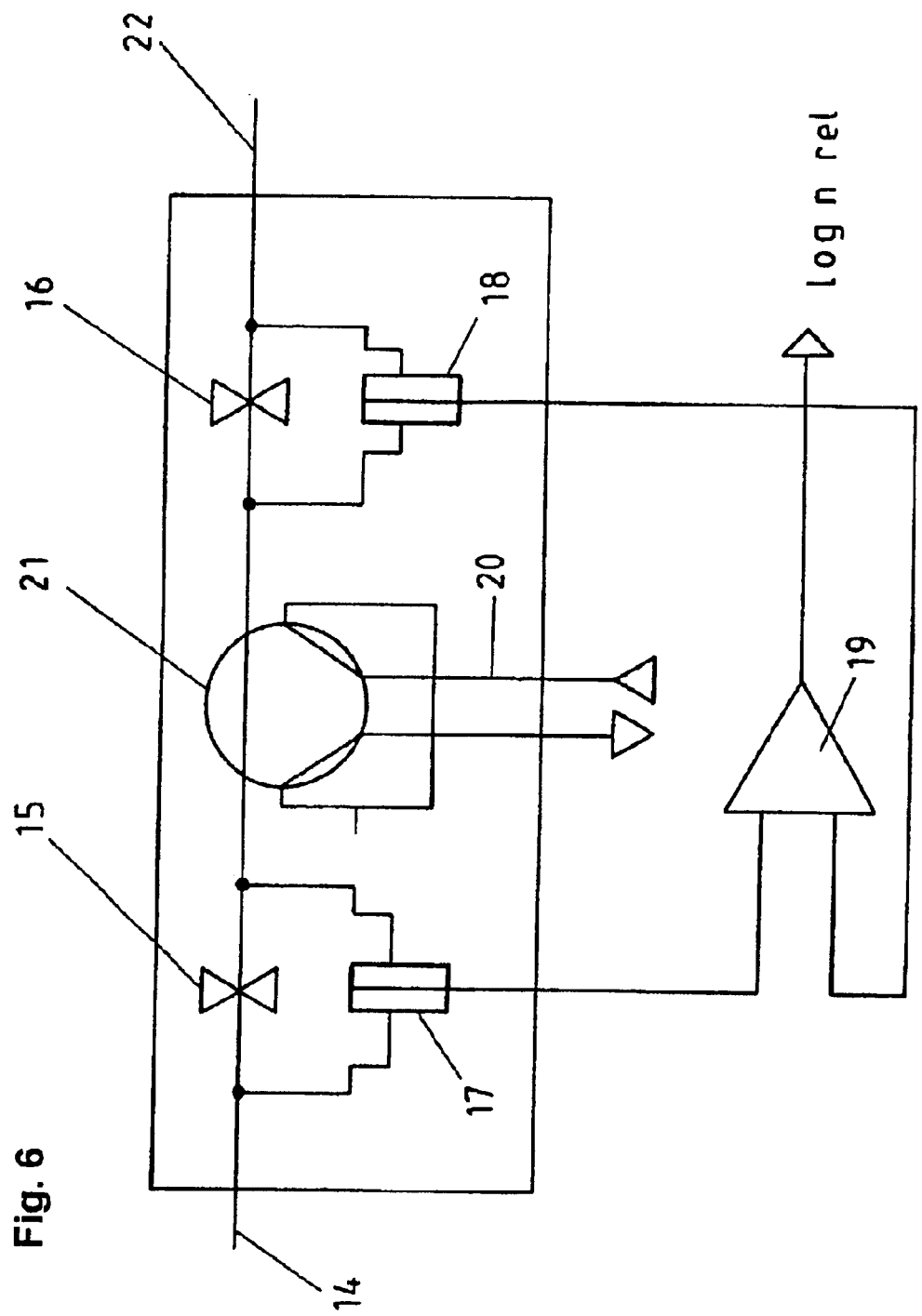
FIGS. 6 to 14 show respectively schematic arrangements of viscosimeters according to the invention.

The arrangement according to FIG. 6 possesses an inlet opening 14 into which the eluent 12 is introduced, eventually after filtration. The lead-through conduit possesses two KV flow resistances placed in series 15 and 16 over which the pressure drop can be respectively measured with pressure sensors 17 and 18. Both values measured by the pressure sensors 17 and 18 are supplied to a differential amplifier 19, are amplified there and treated in the usual manner.

The sample solution is supplied over the supply pipe 20 into the loop of a valve 21. The pressure drop which results because of the flowing through of the pure solvent (eluent) is thus measured at the KV flow resistance 15, while the pressure drop which is caused by a solution composed of solvent and sample is measured on the nozzle body 16. The solution leaves the measuring device by the outlet 22.

Figure 7:
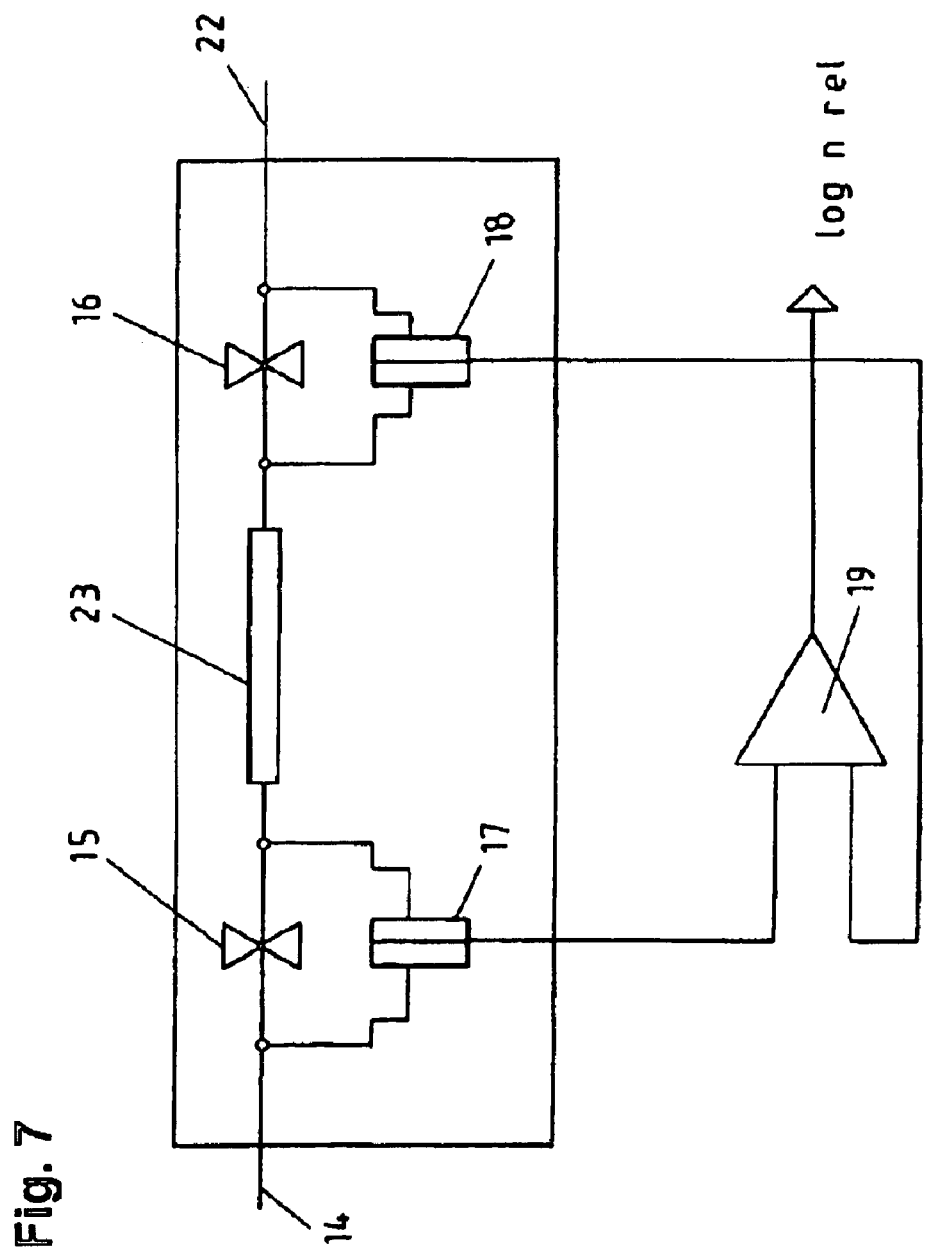

The arrangement represented in FIG. 7 possesses, in contrast to the arrangement described above, a retention basin 23 instead of the loop of the valve 21. Compared with the arrangement described above, the solvent is examined with the sample in the first KV flow resistance 15 which serves here as analytical appliance. If the sample comes into the retention basin 23, it is there considerably diluted and moreover retarded in time in such a way that the KV flow resistance 16 measures only or at least substantially only the solvent. The resistances of this arrangement must not be balanced since their variations do not influence the result.

Figure 8:
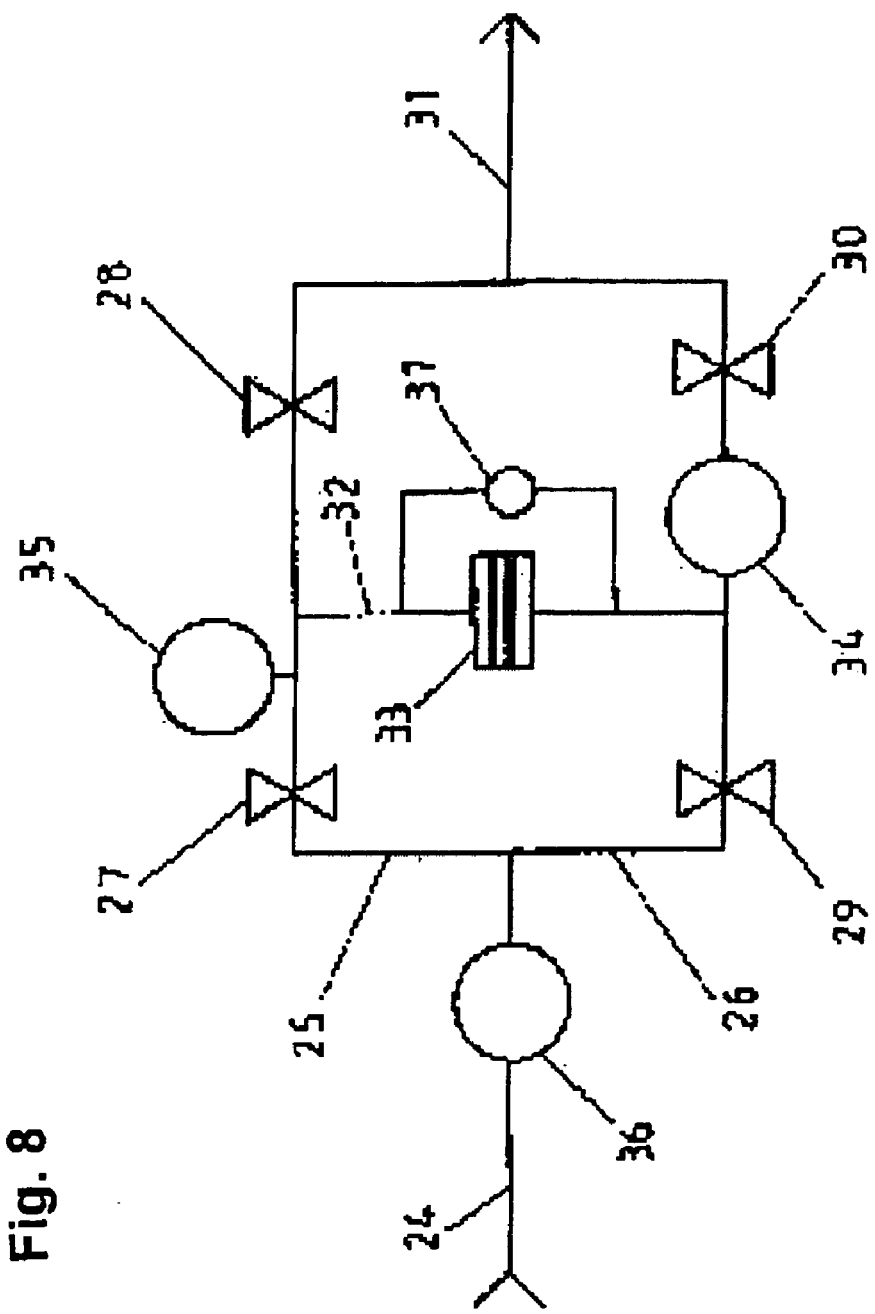

FIG. 8 shows the principally known bridge arrangement for which the supplying conduit 24 is separated into two partial conduits 25 and 26 which have KV flow resistances 27 and 28 or 29 and 30 respectively placed in series. The conduits 25 and 26 join behind the KV flow resistances 28 and 30 to an outlet conduit 31. A bridge conduit 32 with a highly sensitive pressure detector 33 is between the KV flow resistance 27 and 28 on the one hand and the KV flow resistance 29 and 30 on the other hand. Additionally, there are still a retention basin of the above described type in the conduit 26 and a compensating vessel 35 in the conduit 25 before the KV flow resistance 30 for the temperature conditioned expansion of the liquid, this being seen in flow direction, as well as a tank 36 from which the sample solution can be given into the eluate. A safety valve 37 is switched in parallel for the protection of the highly sensitive pressure measuring device 33.

In this bridge arrangement, the KV flow resistances 27 and 29 can be configured for example with the smallest possible thickness while the flow resistances 28 and 30 are configured as capillaries. It is also possible that only 29 is configured as a KV flow resistance and the supplying conduit 25 is placed in as a very long capillary with a big internal diameter, all other parts 27, 28 and 30 being configured as capillaries. In the same way, the parts 27 to 29 can also be configured as KV flow resistance with the smallest possible thickness and the part 30 as a capillary or all parts 27 to 30 as KV flow resistances of the above mentioned type.

The solution displaced through the inlet conduit 24 and with the sample is separated approximately in the ratio 1:1 and flows through the conduits 25 and 26. After having flown through the KV flow resistance 29, the solution is diluted in the retention basin 34 and the pure solvent which is therein is then extruded. But in the leg 25 the solution does not undergo any concentration change so that respectively different pressure drops are registered at the KV flow resistances or capillaries 28 and 30, these pressures drops being measurable by the pressure sensor 33. The measured pressure is proportionate to the viscosity of the sample solution in the measuring leg 25.

Figure 9:
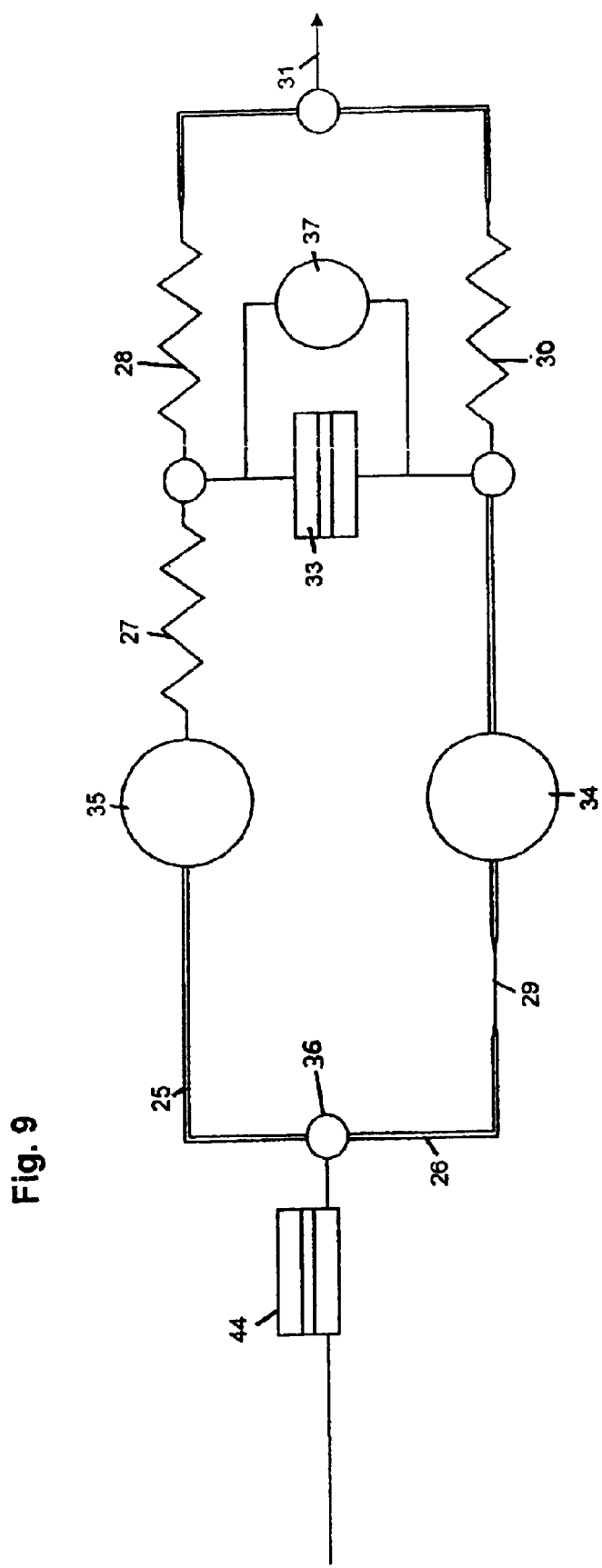

FIG. 9 shows in the inlet conduit an admission pressure sensor 44 which measures the pressure drop over the whole capillary arrangement. In the branch conduit 25, from the branch point with a vessel with a big internal diameter, a dilution vessel 35 and downstream an aforesaid capillary 27 is connected. The second conduit part 26 is comparatively short up to the KV flow resistance 29 in order to run into a dilution vessel 34 downstream of the KV flow resistance 29. The volumes of the vessel and of the supplying capillaries are big in comparison with the volume of the downstream flow resistance 29. The part of the arrangement lying behind the part near the pressure sensor 33 again corresponds to the arrangement of FIG. 8. The working principle of FIG. 9 differs from that of FIG. 8 in that the signal detection takes place completely differently in the front part of the arrangement. As soon as the sample stopper enters the partial leg 26 and reaches the KV flow resistance 30, a signal value is determined, since the sample part which is simultaneously eluted in the partial leg 26 has to flow through the big volume vessels and the dilution vessel 34. Here, the already described dilution and retardation take place so that the rise of pressure recorded in the partial leg 26 is not compensated (as this is the case for the arrangement described in FIG. 8)

but can be measured. The components following behind the diagonal leg (in 33) only serve by appropriately selecting the resistances to fix the distribution ratio of the flow between partial legs 25 and 26. Due to this arrangement, more than 50% of the sample can be used for the further increase of sensitivity.

Figure 10:
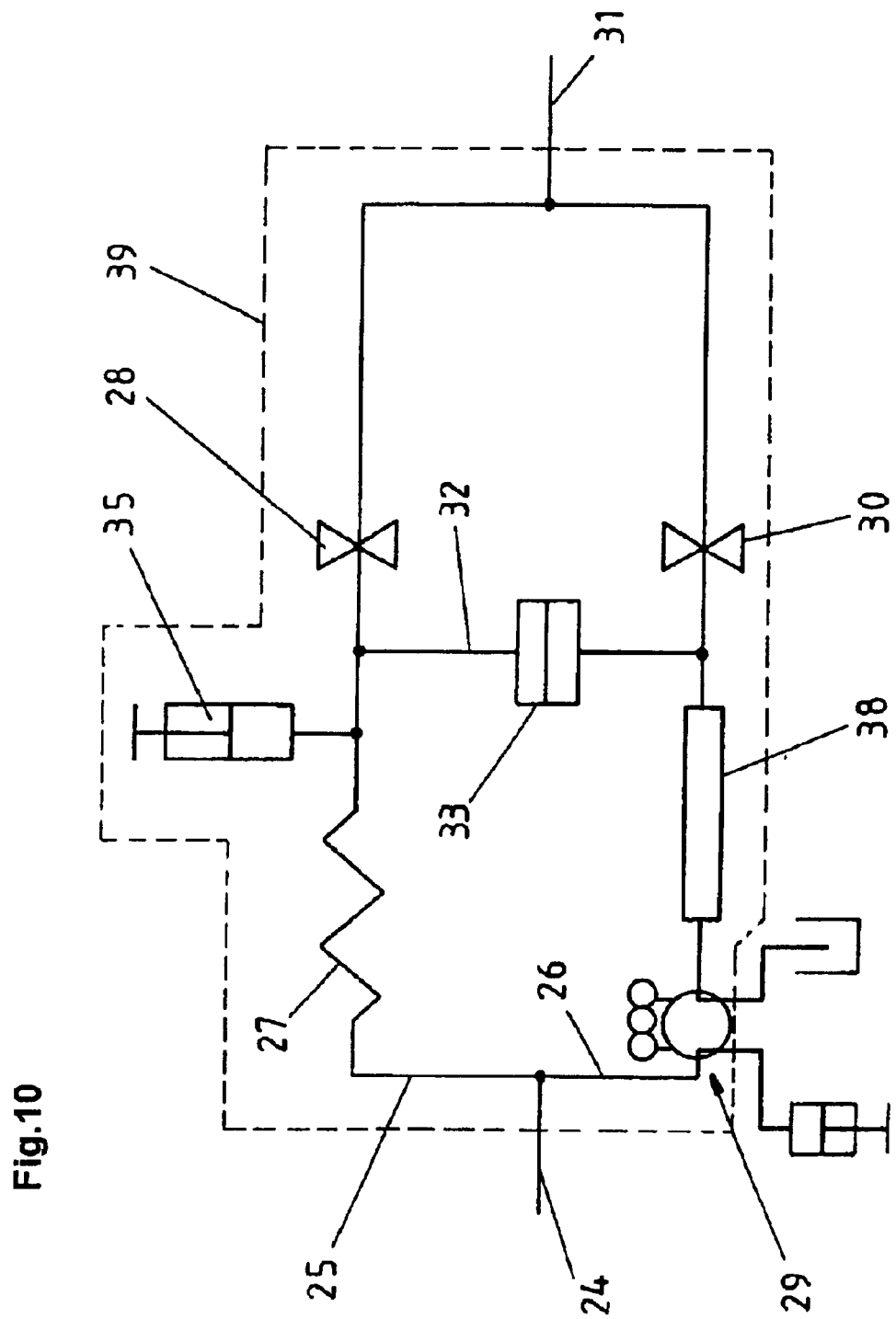

According to FIG. 10 which is substantially constituted like the arrangement according to FIG. 8, a gel permeation chromatograph column 38 is inserted between the first and the second flow resistances 29 and 30 in the leg 26, column from which the polymer stopper emerges and directly enters the taper of the nozzle 30. The pressure drop takes place after the shortest distance, whereby the sample is not enlarged. Preferably, the whole arrangement is in a sealed space 39 which guarantees the constancy of temperature. For the differential measurement carried out, a compensation of the temperature flow fluctuation can eventually be performed, if necessary.

Figure 11:
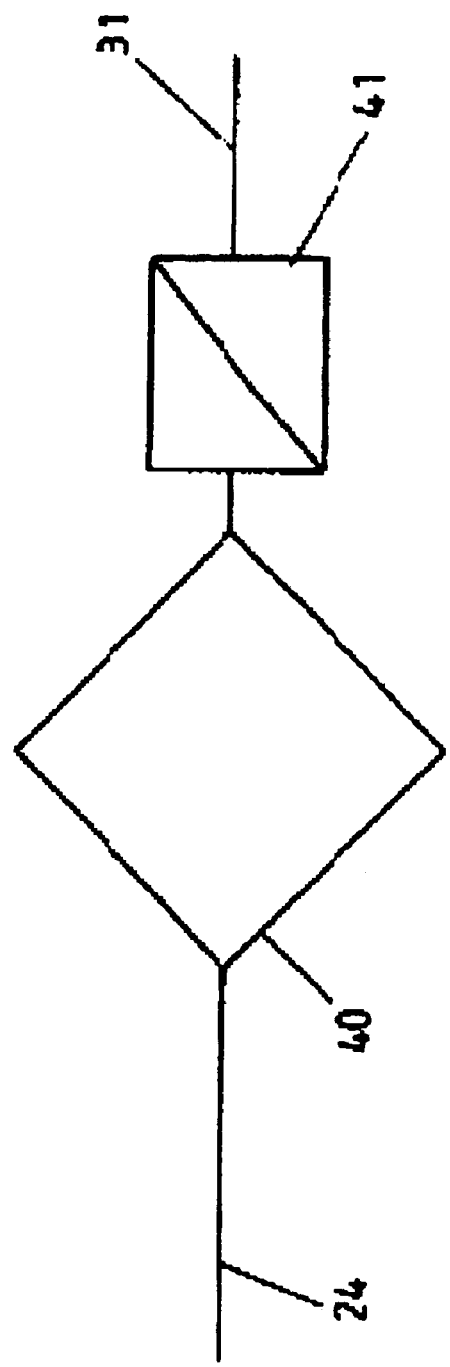
Figure 12:
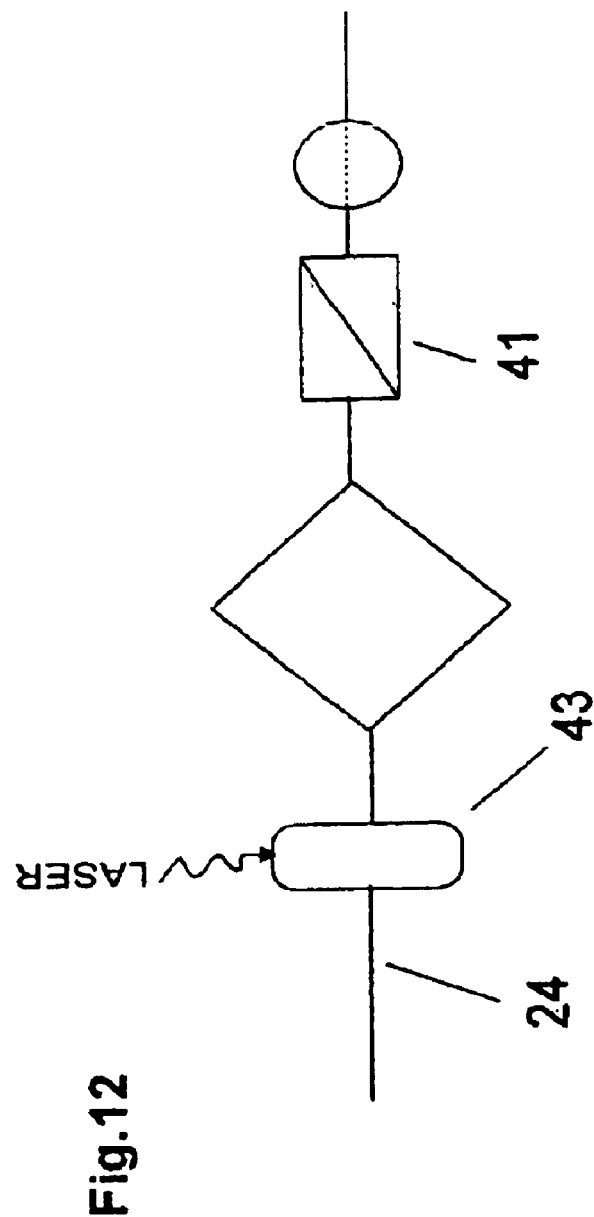
Figure 13:
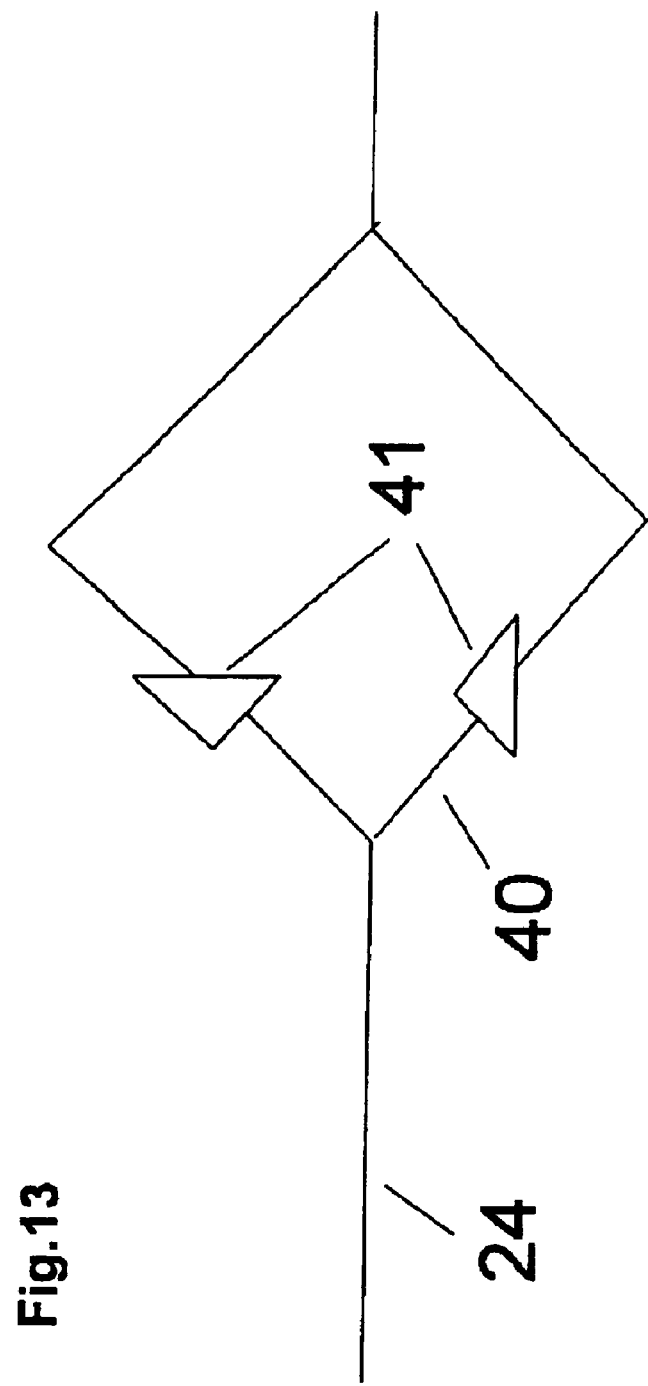
Figure 14:
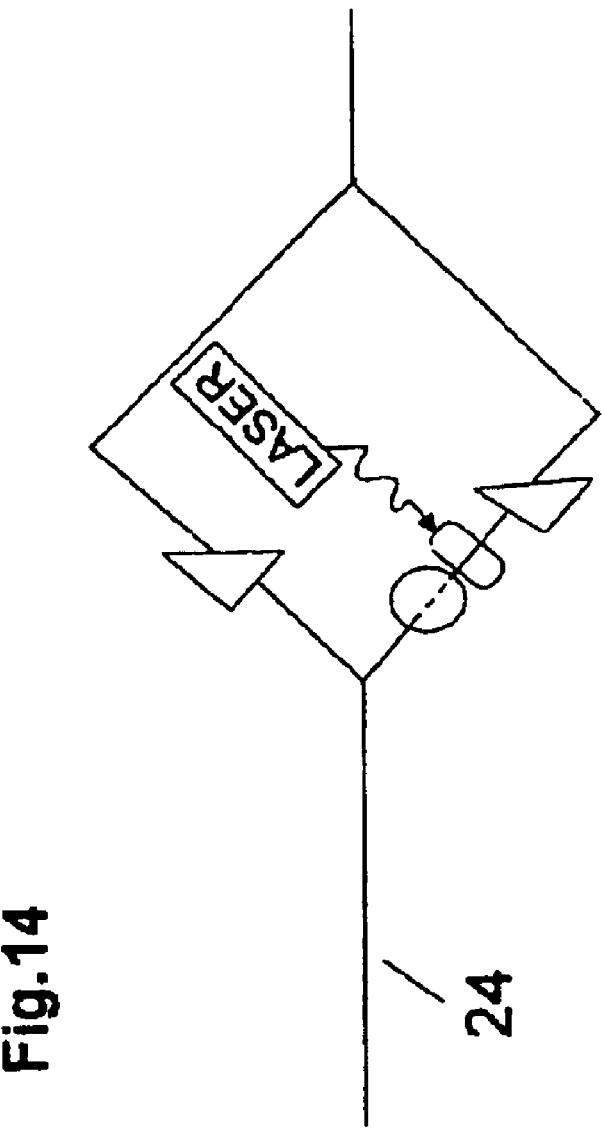

As indicated in FIG. 11, the arrangement 40 represented for example according to one of FIGS. 6 to 14 can also be connected to a refraction detector 41 or basically to further detectors which can give further information about the physical or chemical constitution of the sample. Here, the R1 detector 41 can also be divided and inserted into the two partial legs, as represented in FIG. 13. The same is valid for further detectors such as membrane osmometers, laser scattered light detectors and others C FIG. 12 ).

Furthermore, it is possible to have a block-type arrangement of the detectors, for example, in an arrangement in a row, whereby the first detector is the viscosimeter. By omitting a partial flow, a single-capillary viscosimeter is obtained, whereby a vessel or a container with a comparatively big volume is placed before the measuring capillaries. The pressure measurement is then performed between the big volume vessel and the measuring capillaries. A sufficient quantity of the sample solution is then available in the big volume vessel in order to displace the solvent so that the sample is then conveyed to the first measuring cycle. In this way, high-purity measurements are carried out since the measure is based only exclusively on the sample solution.

Figure 16:
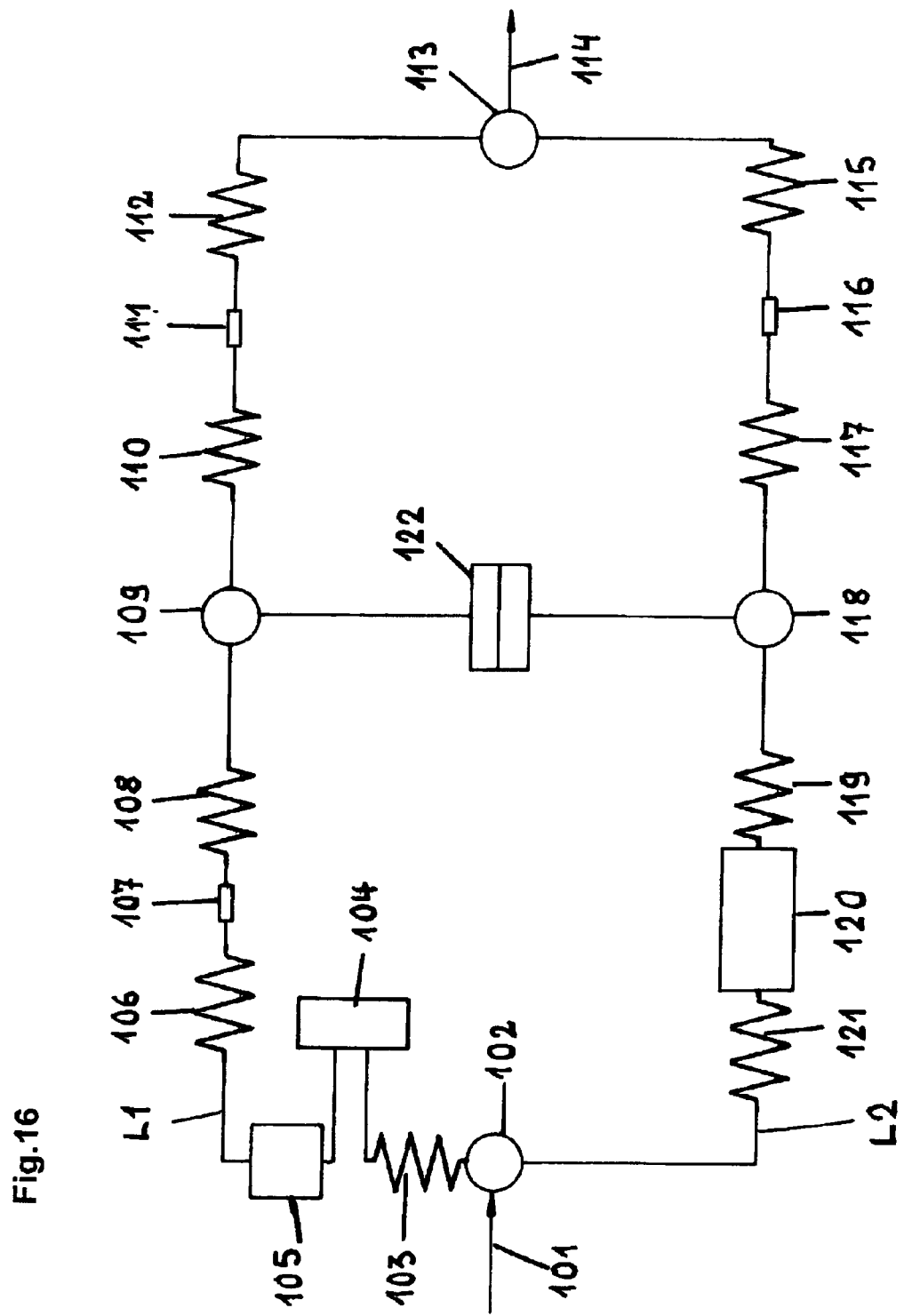
FIG. 16 shows the arrangement in form of a flow chart of a further embodiment of the viscosimeter according to the invention.

According to a further embodiment of the invention according to FIG. 16, an arrangement for a viscosimeter with a flow conduit system with two legs L1, L2 is provided for. The first leg L1 comprises at least three pressure reducing elements, whereby downstream of a capillary 103 following a branch point 102 a pressure manometer 104 with a consecutive bigger vessel 105 is provided for. In the conduit after the branch point 102, further capillaries 106, 108 with different diameters and with big volumes, which are connected by a junction 107, are provided for which correspond to 100 to 1000 times a KV flow resistance 121 in the second leg L2. In the conduit of the leg L1 leading from the branch point 102, a further branch point 109 follows the capillaries 106, 108, this branch point leading to a differential pressure sensor or to a sensor for differential pressure 122. A conduit section with two capillaries 110, 112 with different diameters which are connected with each other by a junction 111 follows this branch point 109. The conduit section of the leg Li which shows the capillaries 110, 112 runs into a junction 113 and from there into an outlet conduit 114. In the other leg L2, the KV flow resistance 121, which is followed by further big volume conduits, follows the branch point 102. The conduit section which receives the big volume conduits and the KV flow resistance 121 leads to a branch point 118 which is connected by a conduit section with the branch point 109, whereby the differential pressure sensor or the sensor for differential pressure 122 is placed. From the branch point 118 in the leg L2, there follows a conduit section which leads to the junction 113 and thus into the outlet conduit 114. Capillaries 115, 117 with different diameters and with different lengths, which are connected with each other by a junction 116, are placed in this conduit section. In this arrangement for the viscosimeter, the liquid supply takes place over the inlet 101 and from the branch point 102 into the leg L1 or into the leg L2. From this branch point 102, a conduit section in the leg L1 leads to the branch point 109. In this conduit section, the capillary 103 is led over a big distance with a comparatively big volume to a manometer (absolute pressure manometer) 104 and from there to a still bigger vessel 105 which is then followed by the conduit section with the two capillaries 106, 108. The two capillaries 110, 112 with different diameters which are connected with each other by a conduit 111 are placed in the conduit section following the branch point 109. From the vessel 105 in the leg L1, a connection conduit leads to a pressure reducing element 106 which is a capillary, a nozzle, a frit or an appropriate device which reduces the pressure in the flow conduit, whereby all other pressure reducing elements which are used can be configured in the same way. This pressure reducing element 106 is connected by the junction 107 with a further capillary 108 with a big volume which runs into the branch point 109, whereby the differential manometer or the manometer for differential pressure 122 placed in the connecting conduit between the two branch points 109, 118 in the two legs L1, L2 is highly sensitive and shows the slightest pressure differences between the two branch points 109, 118 of the flow conduit. The big volume capillary 110 which is placed in the conduit section following the branch point 109 is connected by the junction 111 with a pressure reducing capillary 112, whereby the pressure reduction must not be identical with that in the upper section of the flow conduit.

The conduit branch L2 derives from the branch point 102. The pressure reducing element 121 which can be configured in different ways is placed in this leg L2. The big volume vessel 120 directly follows this pressure reducing element 121, vessel from which a conduit 119 with a big internal diameter then leads to the branch point 118. From this branch point 118, it then leads over the conduit section with the inserted differential manometer or manometer for differential pressure 122 to the branch point 109. In the area of the conduit branch L2, a conduit section leads from the branch point 118 to the outlet conduit 114 and a conduit 117 with a big internal diameter is then provided for in this conduit section. The conduit then leads over the junction 116 to the pressure reducing capillary 115. The differential pressure manometer or manometer for differential pressure 122 is connected in such a way that it generates a positive signal for a pressure drop at the branch point 118. This is also the way how the viscosity signal is generated.

Figure 17:
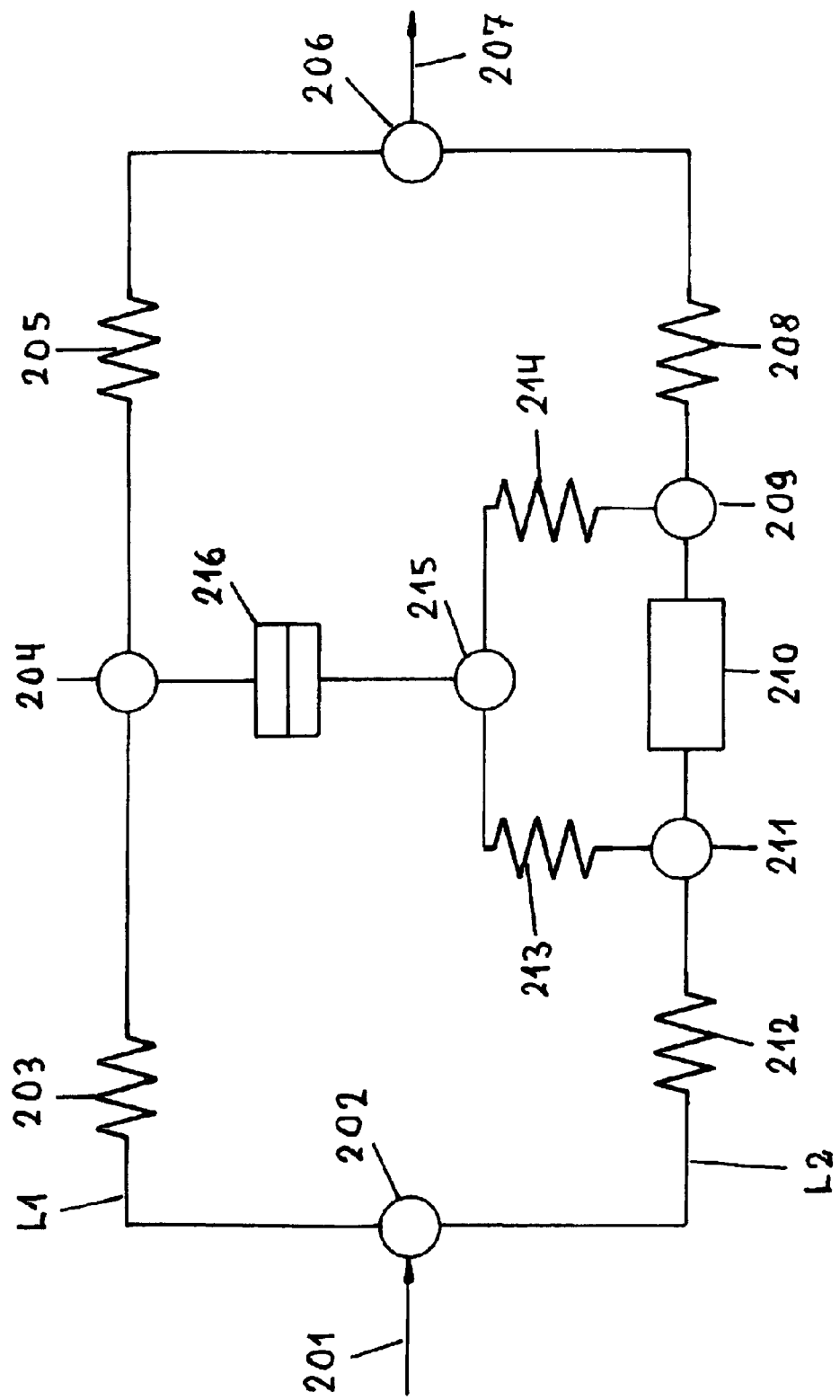
FIG. 17 shows the arrangement in form of a flow chart with three parallel flow circuits of a further embodiment of the viscosimeter according to the invention.

The viscosimeter according to FIG. 17 shows a flow chart different from that of the viscosimeter according to FIG. 16 in so far as three parallel flow circuits are provided for which constitute an analogy with the so-called Thomson bridge. This arrangement stands out in particular in case of low flow rates for which the resistances of supply conduits, even if slight, influence the accuracy of measurement. As shown in FIG. 17, a flow conduit system with two legs L1, L2 is provided for the viscosimeter. This flow conduit system comprises three parallel flow circuits, at least two of them are connected by a differential pressure sensor or a sensor for differential pressure 216. The arrangement itself consists of an inlet 201 which runs into a junction 202 and divides into two legs L1, L2. The leg L1 comprises a conduit section with a pressure reducing element 203, a following branch point 204 and a further pressure reducing element 205. This conduit section runs into a junction 206 with a following outlet conduit 207. The other leg L2 which starts from the branch point 202 comprises a pressure reducing element 212 which is followed by a junction 211. In connection with this junction 211 there follows a big volume vessel 210, whereby a further junction 209 and a pressure reducing element 208 are placed in the following conduit section. This conduit section also leads to the outlet conduit 207. Both junctions 211, 209 are connected over conduit sections with a junction 215 which is again connected with the branch point 204 over a conduit section. The differential pressure sensor or the sensor for differential pressure 216 is placed in this conduit section. A resistance capillary 213, 214 is respectively placed in each of the two conduit sections between the junctions 211 and 209 and the junction 215. A flow conduit system with three parallel flow circuits is obtained on the base of this arrangement.

What is claimed is:

1. A viscosimeter for measuring the relative, intrinsic or inherent viscosity of a solution (13) in a solvent (12) with at least one flow resistance (15, 16; 27 to 30) and one feeding point (20, 21; 36; 38) for the solution to be examined (13) in a conduit system (14, 22; 24 to 26, 31) as well as with respective manometers (17, 18; 33) on the flow resistance (15, 16; 27 to 30) which are coupled with a differential amplifier (19), characterized in that the viscosimeter (40) shows flow resistances (15, 16; 27 to 30) with a minimal thickness and with a smaller volume with respect to all other parallel and following capillaries in a flow conduit system with two legs (L1, L2) which shows three parallel flow circuits among which at least two flow circuits are connected by a differential pressure sensor or a sensor for differential pressure (216), whereby the three flow circuits constitute an analogy to a Thomson bridge, whereby the arrangement consists of an inlet (201) which runs into a first branch point (202) and divides into two legs (L1, L2), whereby the first leg (L1) comprises a first pressure reducing element (203), a second branch point (204) which leads to a differential pressure sensor or to a sensor for differential pressure (216) and a second pressure reducing element (205) in a feeding conduit which leads to a first junction (206) which runs into an outlet conduit (207); and that the second leg (L2) starting from the first branch point (202) comprises a third pressure reducing element (212) which leads to a third branch point (211) which first leads into a big volume vessel (210) leading to a second junction (209) and second which leads to a first resistance capillary (213) which as connected in a third junction (215) with the differential pressure sensor or the sensor for differential pressure (216) and which is furthermore connected with a second resistance capillary (214) in a conduit led from the third junction (215) to a fourth junction (209), whereby the second resistance capillary (214) is connected on the outlet side over the fourth junction (209) with a pressure reducing element (208) which runs over a conduit section into the first junction (206), and thus, into the outlet conduit (207).

2. A viscosimeter according to claim 1, wherein a direct flow opening of the flow resistance is circular or slit-shaped.

3. A viscosimeter according to claim 1, wherein the KV flow resistance shows several hole-type openings of $0.1\mu$ to $150\mu$, whereby the size of each opening depends from the total number of openings.

4. A viscosimeter according to claim 1, wherein in a bridge arrangement in two parallel running flow paths of respectively two or three flow resistances placed in series at least one is configured as the KV flow resistance with the minimal thickness.

5. A viscosimeter according to claim 1, wherein a conduit network (24 to 26, 31) or the legs (L1, L2) are placed in a thermally constant closed space (39).

6. A viscosimeter according to claim 1, wherein a conduit network (24 to 26, 31) or the legs (L1, L2) are placed in a thermally adjustable heat bath.

7. A viscosimeter according to claim 1, wherein the flow resistances are disk-shaped Venturi nozzles.

8. A viscosimeter according to claim 1, wherein the flow resistances are leaf-shaped Venturi nozzles.

* * * * *